United States Patent [19]

Colak

[11] Patent Number: 5,719,398
[45] Date of Patent: Feb. 17, 1998

[54] METHOD AND DEVICE FOR IMAGING THE INTERIOR OF A TURBID MEDIUM

[75] Inventor: Sel B. Colak, Eindhoven, Netherlands

[73] Assignee: U.S. Philips Corporation, New York, N.Y.

[21] Appl. No.: 712,029

[22] Filed: Sep. 11, 1996

[30] Foreign Application Priority Data

Sep. 11, 1995 [EP] European Pat. Off. ............ 95202456

[51] Int. Cl.$^6$ .................................................... G06T 1/00
[52] U.S. Cl. ........................................ 250/341.1; 128/633
[58] Field of Search ................................ 250/341.1, 340, 250/341.7, 332; 128/633, 664, 665; 356/337

[56] References Cited

FOREIGN PATENT DOCUMENTS

WO9107655  5/1991  WIPO .

OTHER PUBLICATIONS

"Monte Carlo Simulations Of Photon Migration Path Distributons In Multiple Scattering Media", Shechao Feng And Fanan Zeng, Spie vol. 1888, pp. 78–89 (Sep. 1993).

"Fundamentals Of Image Processing", A.K. Jain, Prentice Hall, 1989, pp. 439–441.
"Fundamentals Of Image Processing", A.K. Jain, Prentice Hall, 1989, pp. 464–465.

*Primary Examiner*—David P. Porta
*Assistant Examiner*—Richard Hanig
*Attorney, Agent, or Firm*—Jack D. Slobod

[57] ABSTRACT

A method and device of imaging an interior of a turbid medium is disclosed for reconstruction of biomedical images consecutive irradiation of the turbid medium with light from a light source from a plurality of positions and detection of the light propagated along a plurality of paths through the turbid medium. The method starts with a simple back-projection algorithm to get a first image. Then in next steps this image is corrected by deconvolution with a spatially varying convolution function. This convolution function is based on the scattering and coefficients of the turbid medium and the propagation of the light in the turbid medium. A second correction approach is obtained by means of a coordinate transformation. Advantages of the method according to the invention are that the method is rather easy to implement, the method needs only a few iteration steps to obtain corrected images and the method does not suffer from instability problems.

20 Claims, 5 Drawing Sheets

METHOD AND DEVICE FOR IMAGING THE INTERIOR OF A TURBID MEDIUM

BACKGROUND OF THE INVENTION

1. Field of the Invention

The invention relates to a method of imaging an interior of a turbid medium, by consecutive irradiation of the turbid medium with light from a light source from a plurality of positions and detection of the light propagated along a plurality of light paths through the turbid medium, and determination of an image of the interior of the turbid medium from the measured intensities. The invention also relates to a device for carrying out such a method.

2. Description of the Related Art

Such a method is known from the International patent application WO 91/07655. In this patent application, the known method is used for imaging of biological tissue. By "turbid medium" as used herein is meant a volume of a highly scattering substance, for example, an Intralipid solution or biological tissue. It may be possible to use the known method in medical diagnostics for imaging tumors in breast tissue. In the known method an iterative process is used for determining an image of the interior of the turbid medium from the measured intensities. In said iterative process, the measured intensities are compared with calculated intensities of a simulation model incorporating the light source, the interior of the turbid medium, and the detector. The turbid medium is represented as a set of volume elements with associated scattering and/or absorption coefficients in this simulation model. Furthermore, an error function is minimized in the iterative process, which function is determined by the calculated intensities and the measured intensities. The eventual values of the scattering and/or absorption coefficients of the volume elements may subsequently be represented in the form of an image of the interior. A disadvantage of the known method is that this method requires many iterative steps, and accordingly much calculation capacity. Consequently real time imaging is not possible.

SUMMARY OF THE INVENTION

It is among the objects of the invention to provide an image reconstruction algorithm for imaging the interior of the turbid medium with a reduced number of iterative steps. A further object is to render possible a real-time imaging technique for use in medical imaging processes, for example mammography. According to the invention, the method is for this purpose characterized by the following steps:

c) determination of the optical parameters from the measured intensities, d) determination of a first image of the interior of the determined optical parameters by means of a back projection, e) determination of a first spatially varying convolution function from the optical parameters and, f) determination of a second image of the interior of the turbid medium by combining the first spatially varying convolution function and the first image.

The first image is obtained by means of back projection of the determined values of the measured optical parameter. The first image is the blurred version of the second image because the image is convoluted with a normally occurring $1/r$ effect and a spatially varying convolution function. The normal $1/r$ effect occurs upon reconstruction of an object through back projection of measured intensities. The normal $1/r$ effect is negligible relative to the convolution function in the first instance because of the scattering and absorption in the turbid medium. When the $1/r$ effects is not negligible relative to the convolution function in case of strong absorption the $1/r$ effect can be compensated for by applying a band limited filter.

The invention is based on the recognition that a light path distribution function can be used for the description of the propagation of the light through the turbid medium. This light path distribution function is subsequently used for determining the convolution function with which the second image is convolved. It follows from this light path distribution function that the most probable light paths of the light in a homogeneously turbid medium are present mainly within a banana-shaped space or tubular space between a light source and a detector. The light path distribution function is known inter alia from the article "Monte Carlo simulations of photon migration path distributions in multiple scattering media" by S. Feng et al., SPIE vol. 1988, pp. 78–88. The spatially varying parameters of the light path distribution function are determined from the determined optical parameters. Because the back projection and combination are linear operations the order of the back projection and the combination may be reversed. The first image is then formed by the determined intensity values. Further by "light" as used herein is meant electro-magnetic radiation with a wavelength between approximately 200 and 1000 nm.

An embodiment of the method according to the invention is characterized in that the second image is determined by a deconvolution of the first image with the first spatially varying convolution function. One possibility to obtain a second image is to deconvolute the first image with the convolution function in the pseudo-time domain or space domain.

Another embodiment of the method according to the invention is characterized in that the second image is determined by inverse Fourier transform of the quotient of the Fourier-transformed first image and the Fourier-transformed first spatially varying convolution function. An alternative for a deconvolution in the pseudo-time domain is an operation in the frequency or Fourier domain. The advantage of the Fourier domain is that the operations are relatively simple to implement.

An embodiment of the method according to the invention is furthermore characterized by an iterative process in which an $(n+1)^{th}$ image is obtained by carrying out the following steps:

a) determination of an $n^{th}$ spatially varying convolution function from the $n^{th}$ image and the determined optical parameters, and b) determination of the $(n+1)^{th}$-image of the object by combination of the $n^{th}$ image with the $n^{th}$ spatially varying convolution function An iterative process is carried out, in which the $(n+1)^{th}$ improved image of the object is obtained by combining the $n^{th}$ image with a $n^{th}$ convolution function. Two iteration steps are generally sufficient for obtaining an image of good quality. By contrast, many iterations are necessary in the known method, as described in the cited patent application WO 91/07655, The large number of iterations is necessary because only small changes in the absorption and scattering coefficients are possible per iteration otherwise stability problems occur. It is an advantage of the method according to the invention that there no such instabilities in the iteration process occur. The $(n+1)^{th}$ improved image can be determined by inverse Fourier-transform of the quotient of the Fourier-transformed $n^{th}$ image and the Fourier-transformed $n^{th}$ convolution. Alternatively the $(n+1)^{th}$ improved image could be determined by a deconvolution of the $n^{th}$ image with the $n^{th}$ convolution function in the pseudo-time domain or space domain.

An embodiment of the method according to the invention is characterized in that the method includes a step for non-linear coordinate transformation. This correction step can be applied when the difference in the attenuation coefficients of the turbid medium and the attenuation coefficient of an immersed object is large. The correction step compensates for bending of the light rays as a function of the distance from the object. It is remarked that this correction is known from A. Yariv, Quantum Electronics, p 107, 1975 and from H. Schomberg, An improved approach to reconstructive ultrasound tomography, Journal of Physics D., Vol 11, page, 1978. That correction is based on the eikonal equation of geometric optics.

An embodiment of the method according to the invention is characterized in that the optical parameters are the attenuation coefficients. The advantage of using attenuation coefficients is that these attenuation coefficient are easy to obtain from the measured intensities and the known shortest length of a light path. Instead of the attenuation coefficient other optical parameters such as, for example, absorption coefficients, scattering coefficients or diffusing coefficient could be used.

An embodiment of the method according to the invention is characterized in that the method includes a step for reducing high-frequency noise components. In the measuring process and the back projection process high frequency noise components are introduced. These high frequency components could be reduce by a filtering with a low-pass filter. The filtering comprises, for example, the multiplication of a Fourier spectrum of the first image by the frequency response of a low-pass filter or convolution of the image with a two-dimensional impulse response of a low-pass filter.

An embodiment of the method according to the invention is characterized in that the light paths are formed between one light source at a plurality of source positions and one detector at a plurality of detector positions. In this method the turbid medium is irradiated with light from a light source that is consecutive replaced at a number of light source positions after carrying out a range of measurements with one detector at a number of detector positions.

An embodiment of the method according to the invention is characterized in that the light paths are formed between one light source selected from a plurality of light sources located at a plurality of positions and detected by one detector selected from a plurality of detectors at a plurality of positions. This method has the advantage that all the light sources and detector could be in the same fixed mechanical positions relative to the turbid medium, so that mechanical positioning means are not necessary.

An embodiment of the method according to the invention is characterized in that the light paths are formed between one light source at one position and the light is detector by a plurality of detectors at a plurality of positions. This method has the advantage that the number of light sources can be reduced. Mechanical means for positioning the turbid medium relative the light source and the detectors are necessary.

An embodiment of the method according to the invention is characterized in that the light paths are formed between one selected light source out of a plurality of light sources at a plurality of locations and one detector at one position.

The invention also relates to a device, which is provided with:

a) a light source for irradiating the turbid medium, b) a detector for measuring light intensities from light propagated through the turbid medium, c) means for irradiating the turbid medium from a plurality of different positions, d) means for positioning the detector at a plurality of different positions e) a control unit for generating control signals for the devices for positioning the light source and detectors at a plurality of positions, and f) a reconstruction unit for reconstructing an image from the measured intensities, characterized in that the reconstruction unit is equipped for carrying out the following steps:

a) determination of the attenuation coefficients from the measured light intensities, b) determination of a first image of the object from the attenuation coefficient determined sub a) by means of a back projection, c) determination of a first spatially varying convolution function from the attenuation coefficients and, d) determination of a second image by a combination of the first image with the first spatially varying convolution function.

BRIEF DESCRIPTION OF THE DRAWING

The above and other, more detailed aspects of the invention will be explained below by way of example with reference to the drawing.

In the drawing.

DETAILED DESCRIPTION OF THE PREFERRED EMBODIMENTS

Figure 1:
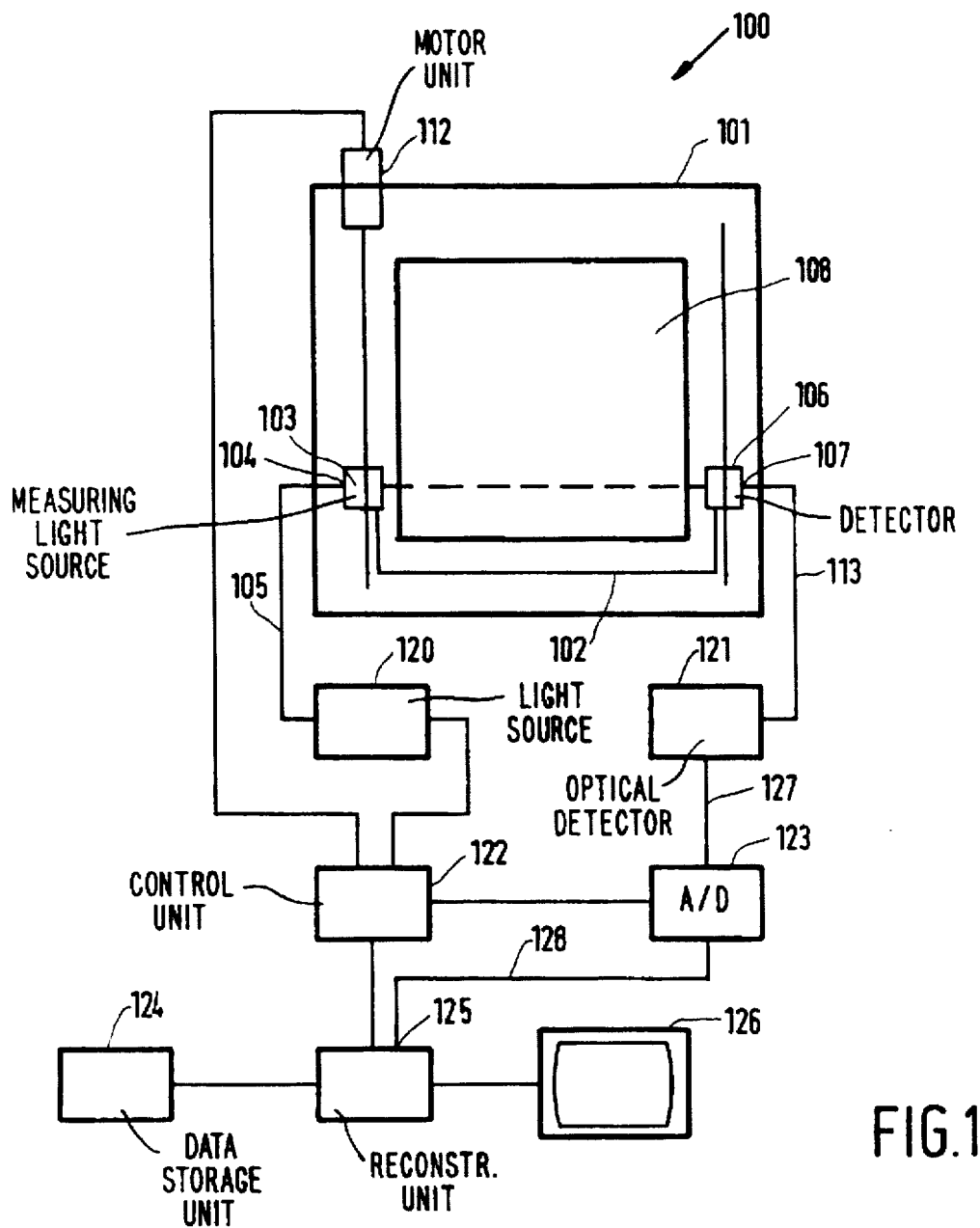
FIG. 1 shows a first device comprising one measuring light source and one detector.

FIG. 1 shows a measuring device 100 for carrying out measurements in a turbid medium in a measuring space 108. The measuring device 100 comprises a measuring light source 103 formed by an output window 104 of a first optical waveguide 105 which is optically coupled to a light source 120, for example a laser diode for generating light with a wavelength of 670 nm and an optical output power of 30 mW. The measuring light source 103 is fastened to a movable slide 102. The moveable slide is mounted on a platform 101. A detector 106 is furthermore arranged opposite the measuring light source 103 on the movable slide 102. The detector 106 is formed by the input window 107 of a second optical waveguide 113 which is optically coupled to an optical detector 121. The optical detector 121 is, for example, a photosensitive PIN diode or a photomultiplier tube. A measuring space 108 in which the turbid medium or biological tissue may be placed is present between the measuring light source 103 and the detector 106. The diameter of the measuring space 108 is, for example, 100 mm. The optical waveguides may be, for example, optical fibers, but an alternative possibility is formed by geometric-optical systems provided with, for example, lenses and mirrors. The movable slide 102 can be set for a number of measuring positions by means of a motor unit 112 which is coupled to a control unit 122. The number of measuring positions lies, for example, between 16 and 256. For carrying out an intensity measurement, the control unit 122 will generate a control signal for the light source 120, so that light is generated in the light source 120. The light of the light source is guided through the first optical waveguide 105 and the output window into the turbid medium in the measuring space 108. The turbid medium comprises, for example, a 1% Intralipid solution in which solution a Delrin cylinder with a radius of 5 mm is immersed. The detector 106 receives a portion of the light transported through the turbid medium in the measuring space 108, and the received light is guided through the second optical waveguide 113 towards the optical detector 121. The optical detector 121 converts the light received into a detector signal. The detector signal is transported to an analog-digital converter 123 via an electrical conductor 127. The detector signal is converted into a digital value I in the analog-digital converter. The digital intensity value I is subsequently passed on to the reconstruction unit 125 through a data bus 128. Data processing takes place in the reconstruction unit 125. The result of the data processing is shown on a monitor 126 in the form of an image, or is stored in a data storage unit 124.

In an embodiment of the method according to the invention, the intensities in M positions are measured in a first direction by means of the detector in a first step, for example, in the X-direction of an orthogonal system of coordinates, and stored in a first data table X(i). The origin of the orthogonal system of coordinates is located at the center of the measurement space 108. In a second step, the intensities are measured in N positions in a second direction, for example the Y-direction of the orthogonal system of coordinates. The number of positions in each direction may lie, for example, between 16 and 256. A practical choice will often be 32. The slide is rotated approximately 90° relative to the turbid medium in the measuring space 108 present between the measuring light source 103 and the detector 106 for measuring in the second direction. The measured intensity values belonging to the second direction are subsequently stored by the reconstruction unit 125 in a second table Y(j). Then a first table of attenuation coefficients $K_x(i)$ and a second table of attenuation coefficients $K_y(j)$ are derived from the measured first intensity table X(i) and the measured second intensity table Y(j) by means of the relation $$\Delta \kappa = \frac{1}{l} \ln\left(\frac{I_i}{I_o}\right), \Delta \kappa = \kappa_0 - \kappa_i \quad (1)$$

wherein l represents the distance between the measuring light source and the detector, $I_i$ the intensity value of the $i^{th}$ detector position, $I_0$ the measured intensity value at a reference position, $K_0$ the background attenuation coefficient at the reference position and $K_1$ the attenuation coefficient at the $i^{th}$ detector position.

Instead of the attenuation coefficient also other optical parameters could be determined, for example, the absorption coefficient, the scattering coefficient or diffuse distance. In addition to this it is also possible to determine differences of the mentioned optical parameters obtained with two consecutive measurements performed with different wavelengths.

In a next step of the method according to the invention, a first image of the interior of the turbid medium is calculated from the first table $K_x(i)$ and the second table $K_y(j)$ by means of back projection. This technique is known for example from computer tomography and described in inter alia "Fundamentals of Image Processing" by A. K. Jain, Prentice Hall, 1989, pp 439–441. The first image is then described by an M×N matrix. A value of an element (i,j) of the matrix $K_0(i,j)$ is determined by the sum of the $i^{th}$ element of the first table $K_x(i)$ and the $j^{th}$ element of the second table $K_y(j)$, so: $K_0(i,j)=K_x(i)+K_y(j)$. After normalization, the first image may be displayed on the monitor 126. In a next step, the determined attenuation coefficients of the table $K_x(i)$ and table $K_y(j)$ serve as a starting point for determining the first image.

It is known from the cited article "Monte Carlo simulations of photon migration path distributions in multiple scattering media" by S. Feng et at., SPIE vol. 1888, pp. 78–88, that the light path distribution function in a homogeneously turbid medium corresponds to a banana-shaped or tubular space between the measuring light source 103 and the detector 106. The light path distribution function $\Phi(r)$ between a detector in position d owing to a point-shaped absorbing particle in location r between a light source and the detector in the turbid medium is then given by $$\Phi(r) = -\frac{aS_0}{4\pi D} \frac{e^{-K|r_s-r|}}{|r_s-r|} \frac{e^{-K|r-r_d|}}{|r-r_d|} \quad (2)$$

wherein r is the distance from a random position of an object to an origin of a system of polar coordinates, $r_s$ the distance from the light source to the origin of the system of coordinates, $r_d$ the distance from the detector to the origin of the system of coordinates, and K is the attenuation coefficient. For tissue-like media the attenuation coefficient can be approximated by $$K = \frac{1}{L_a} = \sqrt{\frac{\mu_a}{D}} - \sqrt{3\mu_a\mu_s'} \;.$$

Here $\mu_a$ is the absorption coefficient and $\mu_s'$ the scattering coefficient, while $L_a$ is the diffuse light penetration depth and D the diffusion coefficient of the turbid medium. For the measuring device as described with reference to FIG. 1, a three-dimensional space is reduced to a two-dimensional space. In addition, the distance between the measuring light source 103 and the detector 106 in the measuring device 100 used is the same for all positions, while a homogeneous turbid medium is presupposed by first approximation. The light path distribution function (2) is now adapted to the orthogonal coordinate system X,Y,Z with the origin located at the center of the measurement space a simplified to the expression $$P(y) = \frac{\exp\left[-2K\sqrt{\left(\left(\frac{l}{2}\right)^2 + y^2\right)}\right]}{\left(\frac{l}{2}\right)^2 + y^2} \quad (3)$$

wherein l is the distance between the light source and the detector, y is the distance from a point y at a line perpendicular to the line l and through the point l/2 and K is the attenuation coefficient. This expression represents the widening of a light path distribution function between a light source and a detector point, given a fixed distance between the light source and the detector, and gives the shape of the convolution function with which the object, i.e. the second image, was convoluted. An example of a banana-shaped light path distribution function is shown in FIG. 2.

Figure 2:
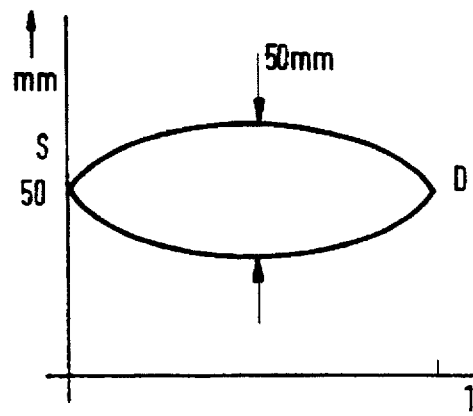
FIG. 2 shows a banana-shaped light path distribution function between measuring light source and detector in a turbid medium.

FIG. 2 shows the contours of a light path distribution function for the value P(0.5) in a homogeneously turbid medium with a value 0.05 mm$^{-1}$ for the attenuation coefficient and a value of 100 mm for the source detector distance. The value P(0.5) indicated that half of the total number photons injected in the turbid medium by the source S will propagate through the turbid medium along a path that will lie in the enclosed area of the banana shape curve. For a turbid medium with a higher attenuation coefficient this banana shape will have a narrower shape and for turbid medium with a smaller attenuation coefficient this banana shape will have a broader shape.

The applied attenuation coefficient of the banana-shaped intensity function (3) is subsequently estimated from the determined attenuation coefficients $K_x(i)$ and $K_y(j)$ through a calculation of the average value of all elements K(i) and K(j), thus:

$$K = \frac{1}{m+n}\left(\sum_{i=1}^{m} K_x(i) + \sum_{j=1}^{n} K_y(j)\right) \quad (4)$$

For highly non linear objects the maximum value of the attenuation coefficients $K_x(i)$ and $K_y(j)$ is used. Highly non linear object are objects with an attenuation coefficient that is approximately 50 times the attenuation coefficient of the turbid medium, in which the object is immersed.

In the method according to the invention, the first spatially varying convolution function is estimated after the first image is back-projected from the attenuation values. Hereto the center of gravity of a recognizable object is estimated from the first image or otherwise available from a priori knowledge. Let this center of gravity be located, for example, at a position $(0,-s_{obj})$, then the first convolution function is given by $G_1(x_i,y_j)=F_1(x_i).F_2(y_j)$, wherein $F_1(x_1)$ is represented by equation(2) for $|r_d - r| =$ $$\sqrt{\left(x_i^2 + \left(-s_{obj} - \frac{l}{2}\right)^2\right)} \; \Lambda|r-r_s| = \sqrt{\left(x_i^2 + \left(-\frac{l}{2} + s_{obj}\right)^2\right)}$$

and $F_2(y_j)$ is represented by equation(2) for $|r_d - r| = \sqrt{\left(y_j^2 + \frac{l^2}{2}\right)} \; \Lambda|r-r_s| = \sqrt{\left(y_j^2 + \frac{l^2}{2}\right)}$ wherein $x_i$ is a coordinate along the X-axis, $y_j$ a coordinate along the Y-axis, K the determined attenuation coefficient (4), l the light source detector distance and $-s_{obj}$ the distance between the recognizable object and the origin O along the negative y-axis. This first convolution function is in principle dependent on the distances of the object to the light source and on the distance of the object to the detector. Therefore it is a spatially varying convolution function. Now the Fourier transform of the first image is equal to the product of the Fourier transform of the second image and the Fourier transform of the first convolution function, so:

$$F\{K_1(i,j)\}=F\{K_2(i,j)\}.F\{G_1(i,j)\}$$

so that the Fourier-transformed second image is equal to:

$$F\{K_2(i,j)\}=F\{K_1(i,j)\}/F\{G_1(i,j)\}.$$

The reconstruction of the second image may also be carried out in an alternative manner, for example through deconvolution in the pseudo-time domain or space domain of the image with a convolution function.

A rapid method of determining the first image is obtained, for example, in the case the area of interest is not too close to the light source or detector. In that case the following steps are carried out in the projection domain:

1. determination of the first table $K'_x(i)$ and the second projection table $K'_y(j)$ from the first image, determination of the Fourier transform of the first and the second projection table, so $F\{K'_x(i)\}$ and $F\{K'_y(j)\}$, and determination of the Fourier transform of a one-dimensional convolution function $F\{G_1(i)\}$, followed by 2. multiplication of the Fourier-transformed data tables as follows:

$$F\{K_{x2}(i)\}=F\{K_{x1}(i)\}/F\{F_1(i)\} \quad (4)$$

$$F\{K_{y2}(i)\}=F\{K_{y1}(i)\}/F\{F_2(i)\} \quad (5)$$

followed by 3. determination of a second image $K_2(i,j)$ by back projection of the table $K_{x2}(i)$ and the table $K_{y2}(j)$.

Any noise present in the first image may be reduced by means of a noise reduction step inserted between steps 2 and 3. In the noise reduction step, the two tables $K_{x2}(i)$, $K_{y2}(j)$ are multiplied by the frequency response H(i) of a noise reduction filter, for example a low-pass filter. After reconstruction by means of back projection and normalization the image can be displayed on the monitor 126.

A further improvement of the image according to the method of the invention can be achieved by means of a non linear coordinate transformation and a next deconvolution step by applying a priori knowledge, e.g. when the difference between the attenuation coefficient of an immersed object and the attenuation coefficient of the surrounding turbid medium is large, for example more then 50 times. The non-linear coordinate transform will be explained with reference to FIG. 8.

Figure 8:
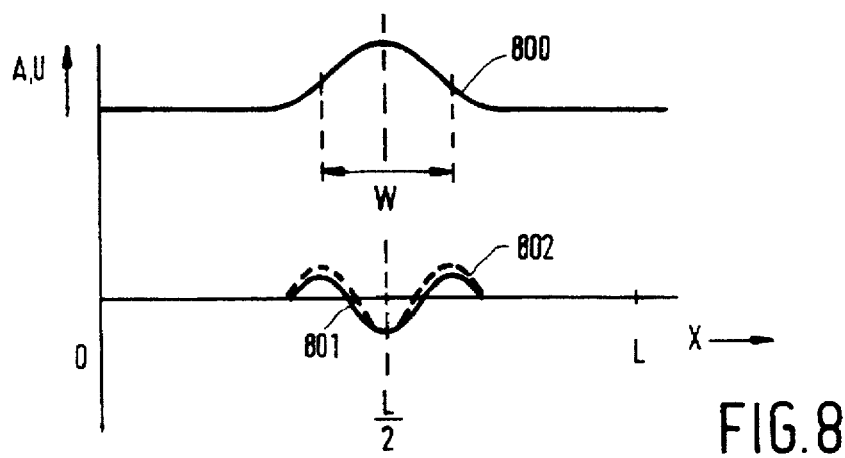
FIG. 8 shows an approximated function to be applied in a non-linear coordinate transformation.

In FIG. 8, a line 800 is shown that represents the attenuation values along a center line of the image $K_2(i,j)$ of an object immersed in a turbid medium. This center line 800 is directed into the direction of the first coordinate axis, for example the X-axis. The attenuation values along the center line are represented by a function S(x). Then a second derivative $S_2(x)$ of this function S(x) to the x variable is obtained. The second derivative $S_2(x)$ is represented in FIG. 8 by the line 801. Then a non-linear coordinate transformation is performed on the first coordinate axis. Hereto the spatial separation $\Delta a$ between two adjacent measurement positions at a position x and x+$\Delta a$, is obtained by dividing the total measurement length L by the number of measured projections M, so $\Delta a=L/M$. The new separation $\Delta a'$, a non homogeneous separation, is now determined by $$\Delta a' = \frac{1}{1+S_2'(x)} \text{ for } x \in \left[\frac{L}{2}-\frac{W}{2}, \frac{L}{2}+\frac{W}{2}\right],$$

wherein $S_2'(x)$ represents an approximated function of $S_2(x)$. In this case this approximated function $S'_2$ is given by one and a halve period of a cosine function, so $$S_2'(x) = A\cos\left(3\frac{\pi}{W}\left(x - \frac{L}{2} + \frac{W}{2}\right) + \frac{\pi}{2}\right),$$

wherein W represents the full width half maximum value of the curve 800. In FIG. 8 the dotted line 802 represents the approximated function $S_2'(x)$. After this non-linear coordinate transform a deconvolution step is performed with the convolution function that was already obtained from equation (3) to determine a third improved image.

Figure 3:
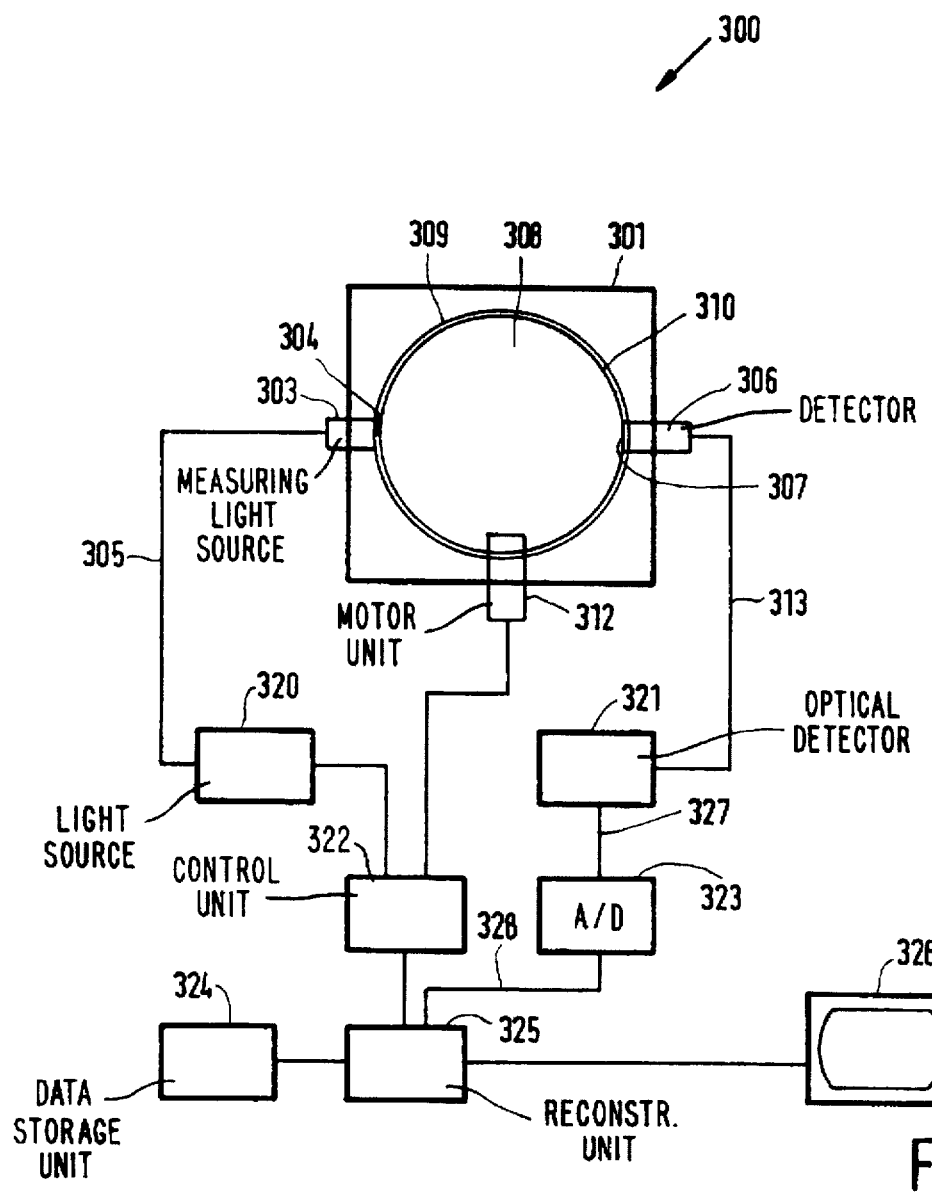
FIG. 3 shows a second device comprising one measuring light source and one detector.

Another arrangement in which an embodiment of the method according to the invention may be used is explained with reference to a measuring device in which the distance between the measuring light source and the detector varies. Such an arrangement is shown in FIG. 3. FIG. 3 shows the measuring light source 303 which is fastened to a first ring 309, and a detector 306 which is placed on a second ring 310. The first ring 309 and the second ring 310 are rotatable relative to one another and are fastened to a platform 301. Furthermore, the measuring light source 303 on the first ring 309 and the detector on the second ring 310 are so fastened relative to one another that the output window 304 of the measuring light source and the input window 307 of the detector 306 lie substantially in one plane. The positions of the measuring light source 303 and of the detector 306 are independently adjustable by means of the motor unit 312. The motor unit 312 is mechanically coupled the first ring 309 and the second ring 310. The first ring 309 and the second ring 310 can be set for a number of measuring positions by means of the motor unit 312 which is coupled to a control unit 322. The number of measuring positions lies, for example, between 16 and 256. A measuring space 308 is present in the center of the first ring 309 and the second ring 310. In this measuring space 308 it is possible to place, for example, a turbid medium containing an object or biological tissue. The diameter of the measuring space is, for example, 100 mm. For carrying out an intensity measurement, the control unit 322 will generate a control signal for the light source 320, so that light is generated in the light source 320. The light of the light source is guided through the first optical waveguide 305 and the output window 304 into the turbid medium in the measuring space 308. The detector 306 receives a portion of the light transported through the turbid medium in the measuring space 108, and the received light is guided through the second optical waveguide 313 towards the optical detector 321. The optical detector 321 converts the light received into a detector signal. The detector signal is transported to an analog-digital converter 323 via an electrical conductor 327. The detector signal is converted into a digital value I in the analog-digital converter. The digital intensity value I is subsequently passed on to the reconstruction unit 325 through a data bus 328. Data processing takes place in the reconstruction unit 325. The result of the data processing is shown on a monitor 326 in the form of an image, or is stored in a data storage unit 324. The following steps are performed for imaging the object in the turbid medium by a second embodiment of the method according to the invention. In a first step, the intensities of the light transported through the turbid medium or the biological tissue are measured consecutively for a first number of M positions of the measuring light source 303, with the detector 306 in a second number of N positions. To this end, the measuring light source 303 is first set in a chosen position by means of the first ring 309 and motor unit 312. The detector position is then rotated through an angle of 360/N° consecutively for each measurement by means of the control unit 322 and the second ring 310. After N measurements the first ring 309 is rotated through 360/M degrees and again M measurement are carried out. The intensity values measured are stored in a table $R_m(i)$ by the reconstruction unit 325. After M×N measurements have been performed, M data tables $R_m$ of N elements each will be available. The data tables are subsequently converted into attenuation coefficient tables $R_m(K_i)$ by means of the relation $$\Delta K = \frac{1}{T} \ln\left(\frac{I_i}{I_o}\right) \quad (6)$$

In a next step, a first image $K_1(i,j)$ is determined from the attenuation tables $R_m(K_i)$ by means of a fan beam back projection. The fan beam back projection is known from inter alia "Fundamentals of Image Processing" by A. K. Jain, Prentice Hall, 1989, pp 464–465. In a next step, a first convolution function is determined from the determined attenuation coefficient table $R_m(K_i)$, but since the distance between the measuring light source 303 and the detector 306 is different now for the various positions of the detector 306 relative to the measuring light source 303, the width of the banana-shaped light path distribution function may be different for each position of the measuring light source 303 and the detector 306. In the method according to the invention, the first convolution function $G_1(i,j)$ is now calculated in that an element of the first convolution function $G_1(i,j)$ is calculated from the starting point that the attenuation coefficients belonging to the light paths $L_{s,d}$ between the M measuring light source positions and N detector positions for each element (i,j) multiplied with the probability that the light will pass a point i,j in an orthogonal two-dimensional space containing the source and detector positions, by means of the relation:

$$K'(i,j) = \frac{\sum_{q,r=1}^{M,N} \kappa(q,r)P_{q,r}(i,j)}{\sum_{q,r=1}^{M,N} P_{q,r}(i,j)} \quad (7)$$

wherein $P_{q,r}(i,j)$ is the light path distribution function between a measuring light source position $S_q$ and a detector position $D_r$, which light path distribution function is influenced by a infinitesimal small absorbing particle at location i,j. Where $P_{q,r}(i,j)$ can be derived from equation (2).

This calculation of the attenuation coefficient related to an element i,j is illustrated with reference to FIG. 4.

Figure 4:
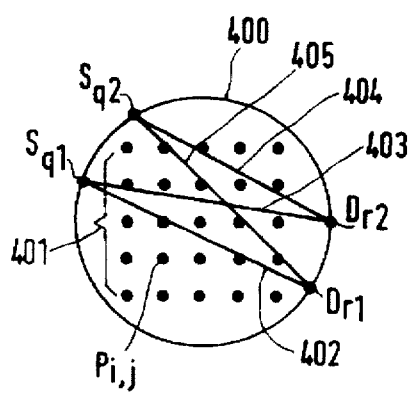
FIG. 4 shows the possible light paths between 2 measuring light source detector pairs.

FIG. 4 shows two measuring light sources at locations $S_{q1}$ and $S_{q2}$ and two detectors at locations $D_{r1}$ and $D_{r2}$, both detector and measuring light source locations are placed at a circle 400. Further an array of points $P_{ij}$, for example a 5×5 array 401, is located within the circle 400. Each point i,j of the array 401 corresponds with the element i,j of a convolution matrix I. The attenuation coefficient corresponding to the element $_{ij}$ of the first convolution function is now given by the summation of the attenuation coefficients of the light path distributions between all the possible measuring light source and detector light paths multiplied by the probability that a light path will pass the point $P_{ij}$. FIG. 4 shows four shortest possible light paths 402,403,404,405, between the two measuring light sources $S_{q1},Q_{q2}$ and the two detectors $D_{r1},D_{r2}$. For these two measuring light sources at location $S_{q1},S_{q2}$ and these two detectors at location $D_{r1}$ and $D_{r2}$ the calculation of the attenuation coefficient results in $$K(i,j) = $$

$$\frac{K_{q1,r1}P_{q1,r1}(i,j) + K_{q2,r2}P_{q2,r2}(i,j) + K_{q1,r2}P_{q1,r2}(i,j) + K_{q2,r1}P_{q2,r1}(i,j)}{P_{q1,r1}(i,j) + P_{q2,r2}(i,j) + P_{q1,r2}(i,j) + P_{q2,r1}(i,j)}$$

wherein $P_{q,r}(i,j)$ is given by equation (2).

In a next step, after determination of the first convolution function, a first image is reconstructed in that the following sub-steps are carried out in the frequency domain:

1. determination of a Fourier transform of the first image $F\{K_1(i,j)\}$, and determination of the Fourier transform of the first convolution function $F\{G_1(i,j)\}$, followed by
2. determination of the Fourier transform of the second image $F\{K_2(i,j)\}$ by $F\{K_2(i,j)\}=F\{K_1(i,j)\}/F\{G_1(i,j)\}$ followed by
3. determination of a second image $K_2(i,j)$ by means of an inverse Fourier transform of $F\{K_2(i,j)\}$.

If so desired, any noise present may be reduced in a next step, i.e. an additional filtering step, before the inverse Fourier transform of the image $F\{K_2(i,j)\}$ is carried out, for example, with the use of a low-pass filter through multiplication of $F\{K_1(i,j)\}$ by a frequency response $H(i,j)$ of the low-pass filter. Another embodiment of the method may be used in yet another measuring device in which the distance between the measuring light source and the detector also varies. This embodiment of the method is explained with reference to FIG. 5.

Figure 5:
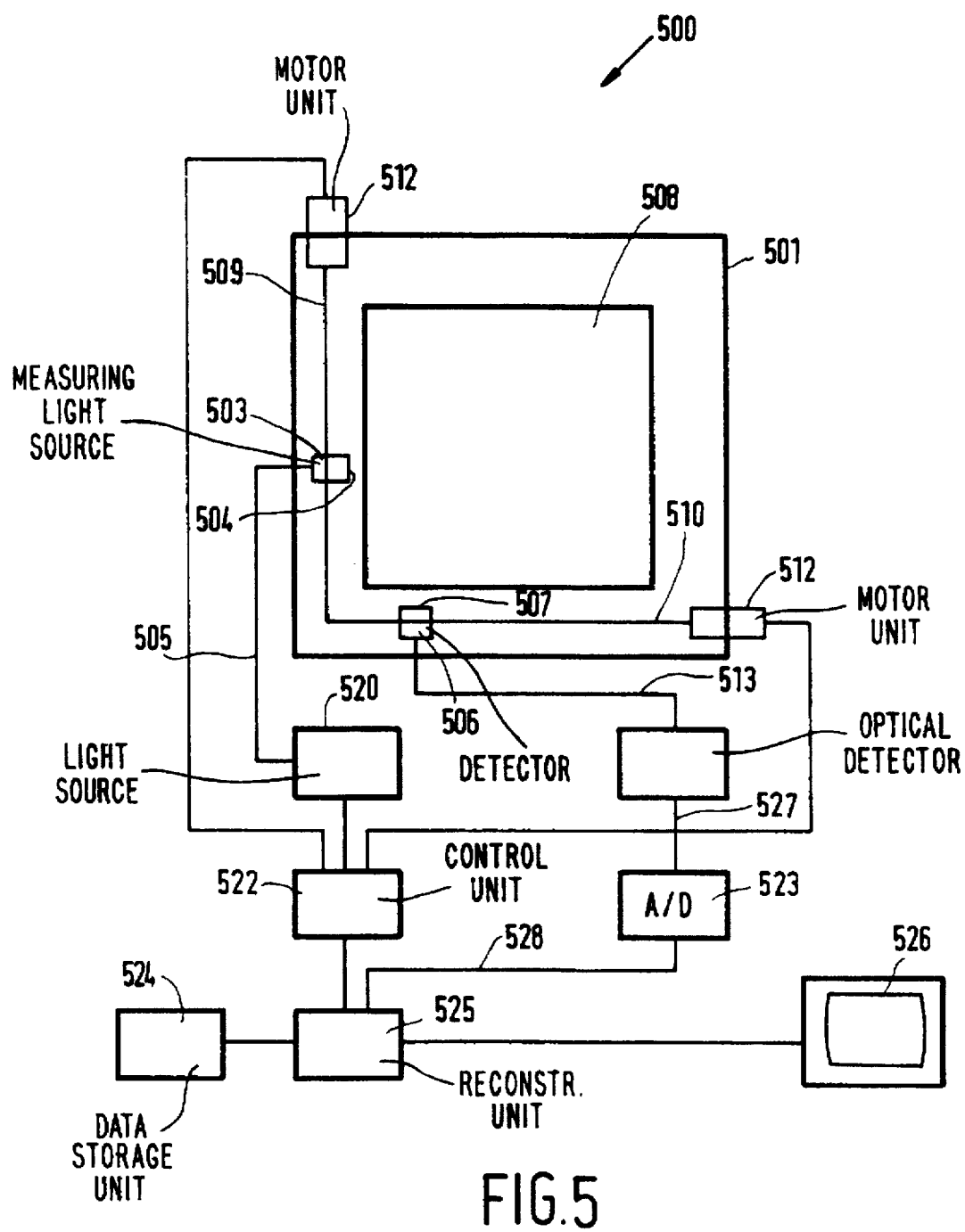
FIG. 5 shows a third device comprising one measuring light source and one detector.

FIG. 5 shows a measuring device 500 comprising a first slide 509 for the measuring light source 503, a second slide 510 for a detector 506, the two slides enclosing an angle α with one another of, for example, 90°. The first slide 509 and the second slide 510 are also moveable relative to one another and are mounted at a platform 501. Furthermore, the measuring light source 503 and the detector 506 on the first slide 509 and the second slide 510 are so fastened relative to one another that the output window 504 of the measuring light source 503 and the input window 507 of the detector 506 lie substantially in one plane. The positions of the measuring light source 503 and of the detector 506 are independently adjustable by means of the motor unit 512. The first slide 509 and the second slide 510 can be set for a number of measuring positions by means of a motor unit 512 which is coupled to a control unit 522. The number of measuring positions lies, for example, between 16 and 256. A measuring space 508 is present between the first slide 509 and the second slide 510. In this measuring space 508 it is possible to place, for example, a turbid medium or biological tissue. The diameter of the measuring space is, for example, 100 mm. For carrying out an intensity measurement, the control unit 522 will generate a control signal for the light source 520, so that light is generated in the light source 520. The light of the light source is guided through the first optical waveguide 505 and the output window 504 into the turbid medium in the measuring space 508. The detector 506 receives a portion of the light transported through the turbid medium in the measuring space 508, and the received light is guided through the second optical waveguide 513 towards the optical detector 521. The optical detector 521 converts the light received into a detector signal. The detector signal is transported to an analog-digital converter 523 via an electrical conductor 527. The detector signal is converted into a digital value I in the analog-digital converter. The digital intensity value I is subsequently passed on to the reconstruction unit 525 through a data bus 528. Data processing takes place in the reconstruction unit 525. The result of the data processing is shown on a monitor 526 in the form of an image, or is stored in a data storage unit 524. The intensities $I_0$ are again measured in M positions of the measuring light source and N positions of the detector and listed in a table $P_m(i)$, and converted into attenuation coefficient tables $P_m(k_i)$ by means of the equation:

$$\Delta \kappa = \frac{1}{T} \ln\left(\frac{I_i}{I_o}\right).$$

In the method according to the invention, $G_1(i,j)$ is calculated again for each element $(i,j)$ in an orthogonal two-dimensional space from the attenuation coefficients belonging to the light paths $L_{s,d}$ between the M measuring light source positions and the N detector positions by means of the summation (7). These attenuation coefficients directly determine the first convolution function $G_1(i,j)$, with which the second image was convoluted. In a next step, a second image is reconstructed in that the following sub-steps are carried out in the frequency domain:

1. determination of a Fourier transform of the determined attenuation coefficients $F\{K_1(i,j)\}$, and determination of the Fourier transform of the first convolution function $F\{G_1(i,j)\}$, followed by
2. determination of the Fourier transform the second image $F\{K_2(i,j)\}$ by $F\{K_2(i,j)\}=F\{_1(i,j)\}/F\{G_1(i,j)\}$, followed by
3. determination of a second image $K_2(i,j)$ by means of an inverse Fourier transform of $F\{K_2(i,j)\}$.
4. reconstruction of the second image $K_2(i,j)$ by means of fan beam back projection of $K_2(i,j)$.

In this embodiment of the method the back projection is carried out after deconvolution of the dam. If so desired, any noise present may be reduced in a next step, i.e. an additional filtering step, before the inverse Fourier transform of the image $F\{K_2(i,j)\}$ is carried out, for example, with the use of a low-pass filter through multiplication of $F\{K_2(i,j)\}$ by a frequency response $H(i,j)$ of the low-pass filter.

Figure 6:
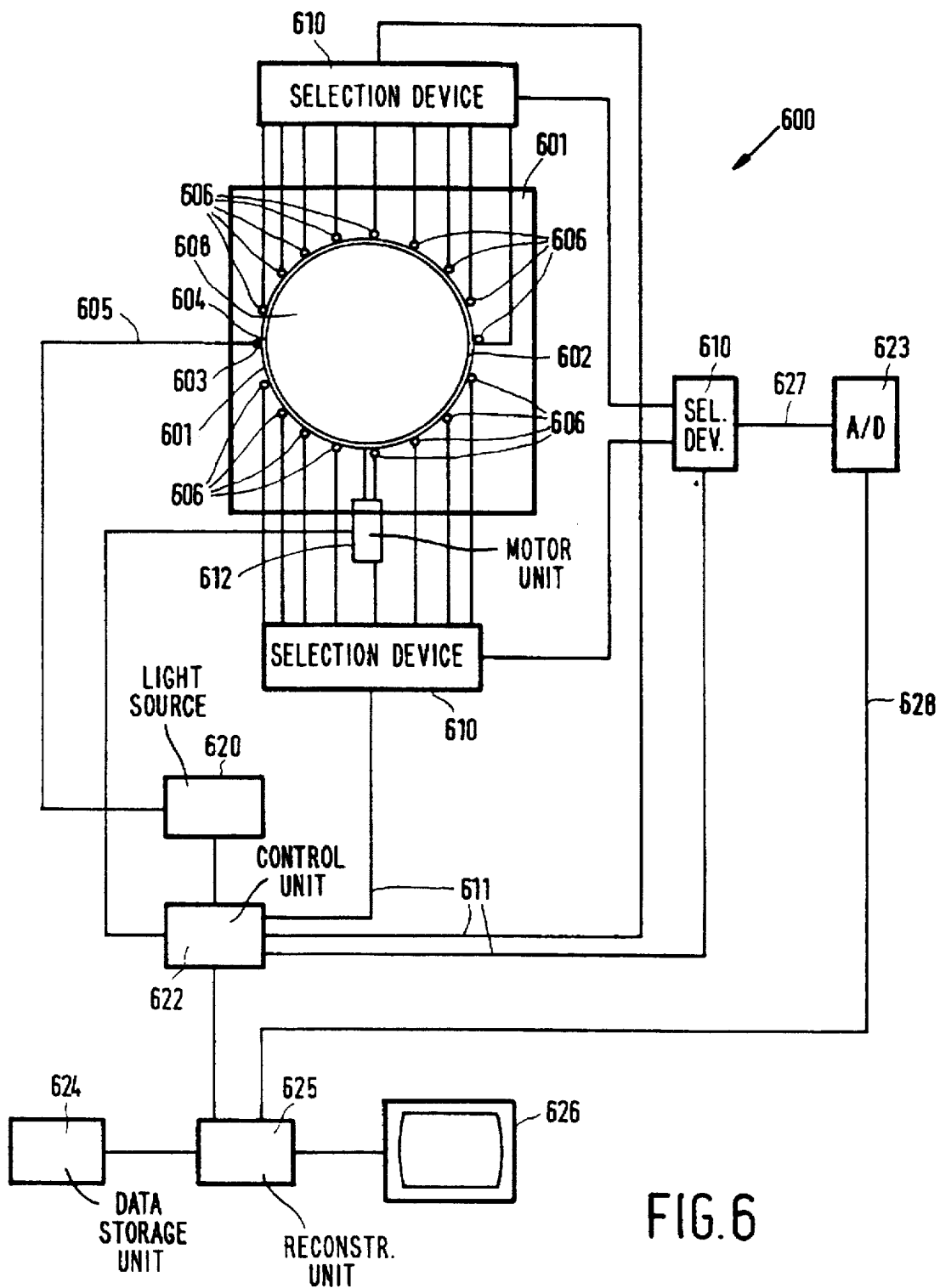
FIG. 6 shows a fourth device comprising one measuring light source and a plurality of detectors.
Figure 7:
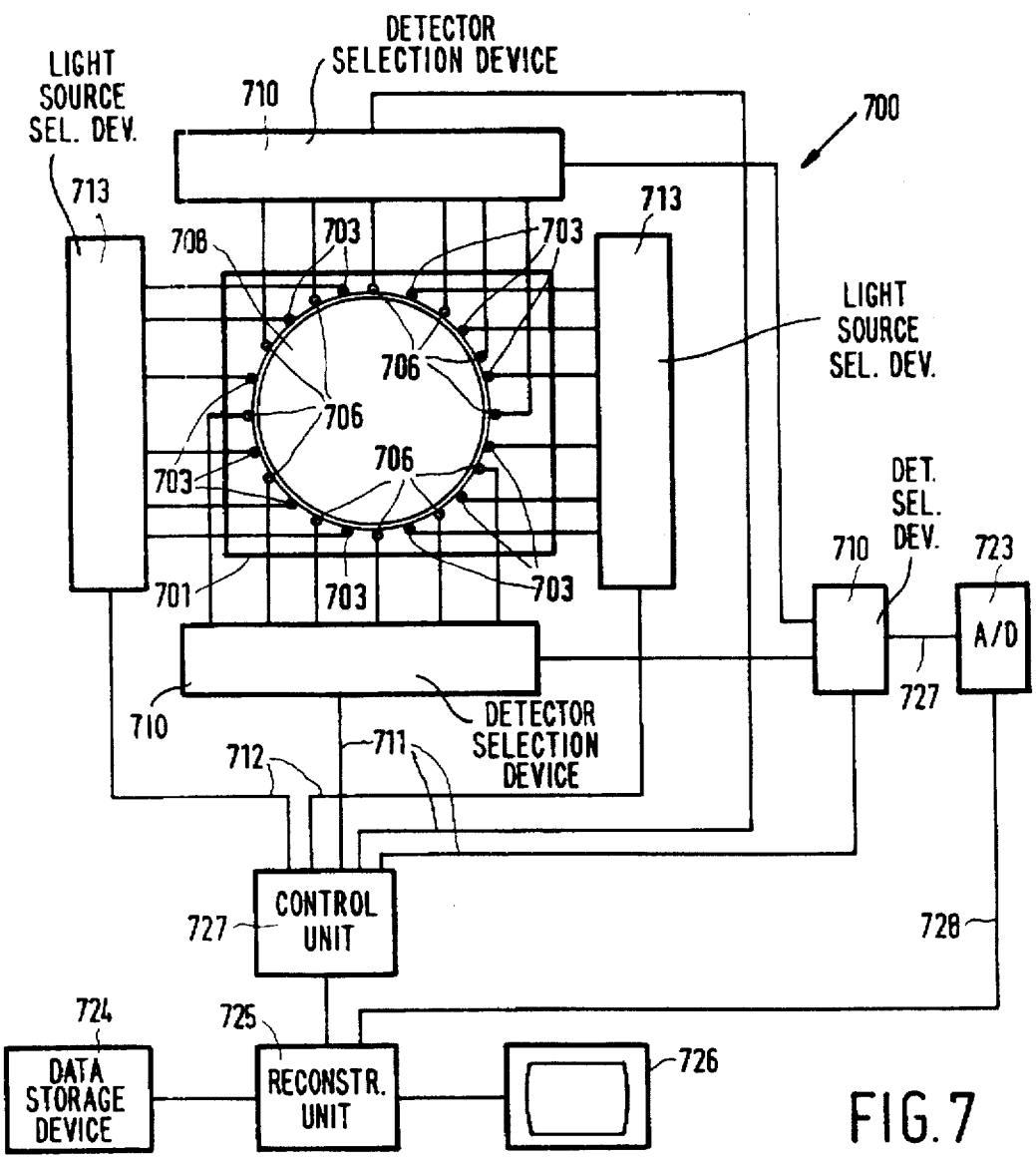
FIG. 7 shows a fifth device comprising a plurality of measuring light sources and a plurality of detectors.

It should be noted that instead of a measuring device with only one measuring light source and one detector, measuring devices may alternatively be used which comprise one measuring light source and a plurality of detectors. Such an embodiment is illustrated with reference to FIG. 6. FIG. 6 shows a measuring device 600, comprising a measuring light source 603 and a number of detectors 606 placed at equal distances at a circle on a platform 601. The detectors 606 are, for example, PIN-photodiodes. The turbid medium in the measuring space 608 is placed at a table 602 located in the center of the circle into the platform 601. The table 602 can be rotated in a number of angular positions with relation the light source 603 by means of a motor unit 612. The number of angular positions may vary between 16 and 256 positions, for example 32 positions. The motor unit 612 is controlled by a control unit 622. Further the control unit 622 selects one out of the N detectors 606 by controlling the selection devices 610 by the selection signals 611, wherein the number of detectors N has a value between 16 and 64, for example 32. As a result of this selection a intensity signal 613 that represents the value of the intensity on the selected detector 606 is supplied to the A/D converter 623. For carrying out an intensity measurement the control unit 622 generates a control signal for the light source 620, so that light is generated in the light source 620. The light of the light source 620 is guided to a first optical wave guide 605 and the output window 604 into the turbid medium in the measuring space 608. The detectors 606 receive a portion of the light propagated through the turbid medium in the measuring space 608. The detectors 606 convert the received light into detector signals. The detector signal are passed to selection devices 610. The control unit 622 selects alternately one out of all the detector signals by means of the selection devices 610 by generating selection signals 611. The selected detector signal is passed to an A/D-converter 623 by the electrical conductor 627. This A/D-converter 623 converts the detector signal to a digital intensity value I. The digital intensity value I is subsequently passed on to the reconstruction unit 625 through a data bus 628. The measured intensities are then stored in an intensity table $P_m(i)$ in the reconstruction unit 625. After measurement of all the intensities of the detectors in one position the table is rotated to a next angular position, which is rotated an angle 360/M towards the former angular position, wherein M is the number of angular positions of the table that are measured for a complete measurement of the turbid medium. After the measurement step a table of M×N intensities is available for further processing and reconstruction in the reconstruction unit 625. The further processing is similar with the processing steps as described in the description of FIG. 2. After reconstruction the image could be displayed on a monitor 626 or stored at data storage unit 624. Another embodiment closely related to this embodiment is a nearly similar device comprising one detector 606 and a plurality of measuring of light source 503. In this device the control unit selects one measuring light source out of the plurality of measuring light sources. In a next embodiment of the invention a plurality of measuring light sources and a plurality of detectors is applied. A method according the invention with such a measurement device is explained with relation to FIG. 7. FIG. 7 shows a another measuring device 700, which measuring device comprises a plurality M of measuring light sources 703 and a plurality N of detectors 706 placed at equal distances at a circle on a platform 701 around an turbid medium place in a measuring space 708. In this embodiment the light sources 703 comprise, for example, a light emitting diode and the detectors comprise, for example, a PIN photodiode. For carrying out a measurement the control unit 722 selects one measuring light source 703 out of the M measuring light sources 703 by means of light source selection devices 713 and one detector out of the N detectors by means of detector selection devices 710 by generating of a light source selection signal 712 and a detector selection signal 711. The selected detector signal is passed to an A/D-converter 723 by the electrical conductor 727. This A/D-converter 723 converts the detector signal to a digital intensity value I. The digital intensity value I is subsequently passed on to the reconstruction unit 725 through a data bus 728. The result of an intensity measurement of a selected measuring light source 703 by consecutive selected detectors 706 is stored in a table $P_m(i)$ of intensity values in the reconstruction unit 725. The complete measurements from all possible measuring light sources results in an array of P(i,j) intensity values. This intensity array P(i,j) is available for further processing in the reconstruction unit 725. After reconstruction an image can be displayed on the monitor 726 or stored in a storage unit 724. The method of processing is similar as the method as described in the description of FIG. 2

Further all other geometries of source and detector positions could be used as far as the distances between all the source detector pairs are known. Consequently the shape of the measuring space 108 could be accommodated to the shape of the human breast to be able to image the human breast tissue.

I claim:

1. A method of imaging an interior of a turbid medium comprising:
    a) consecutively irradiating the turbid medium with light from a light source from a plurality of positions and detection of the light propagated along a plurality of light paths through the turbid medium to measure intensities,
    b) determining an image of the interior of the turbid medium from the measured intensities, characterized in that the following are carried out for determining the image of the interior of the turbid medium:
    c) determining optical parameters from the measured intensities,
    d) determining a first image of the interior of the turbid medium from the determined optical parameters by means of a back projection,
    e) determining a first spatially varying convolution function from the optical parameters, and
    f) determining a second improved image of the interior of the turbid medium by combining the first spatially varying convolution function and the first image.

2. A method as claimed in claim 1, characterized in that the second image is determined by a deconvolution of the first image with the first spatially varying convolution function.

3. A method as claimed in claim 1, characterized in that or the second image is determined by inverse Fourier transform of the quotient of the Fourier-transformed first image and the Fourier-transformed first spatially varying convolution function.

4. A method as claimed in claim 1, characterized in that the following steps are carried out for obtaining an $(n+1)^{th}$ improved image in an iterative process, in which process the following steps are performed:
    a) determination of an $(n+1)^{th}$ spatially varying convolution function from the $n^{th}$ image and the optical parameters, and
    b) determination of the $(n+1)^{th}$-image of the object by a combination of the $n^{th}$ image with the $n^{th}$ spatially varying convolution function.

5. A method as claimed in claim 4, characterized in that the method includes a step for non-linear coordinate transformation.

6. A method as claimed in claim 1, characterized in that the optical parameters are attenuation coefficients.

7. A method as claimed in claim 1, characterized in that the method includes a step for reducing high-frequency noise components.

8. A method as claimed in claim 1, characterized in that the light paths are formed between one light source at a plurality of source positions and one detector at a plurality of detector positions.

9. A method as claimed in claim 1, characterized in that the light paths are formed between one light source selected from a plurality of light sources located at a plurality of positions and detected by one detector selected from a plurality of detectors at a plurality of positions.

10. A method as claimed in claim 1, characterized in that the light paths are formed between one light source at one position and a one detector selected out of a plurality of detectors at a plurality of positions.

11. A method as claimed in claim 1, characterized in that the light paths are formed between one light source selected from a plurality of light sources at a plurality of positions and one detector at one position.

12. A device for imaging an interior of a turbid medium, which is provided with:
   a) light source means for irradiating the turbid medium,
   b) detector means for measuring light intensities from light propagated through the turbid medium,
   c) means for irradiating the turbid medium with light from the light source means from a selected one of a plurality of different positions,
   d) means for receiving light whose intensity is to be measured by the detector means at a selected one of a plurality Of different positions,
   e) a control unit for generating control signals for the irradiating means and the receiving means, and
   f) a reconstruction unit for reconstructing an image from the measured intensities, characterized in that the reconstruction unit comprises means for:
   a) determining attenuation coefficients from the measured light intensities,
   b) determining a first image of the object from the attenuation coefficients by means of a back projection,
   c) determining a first spatially varying convolution function from the attenuation coefficients, and
   d) determining a second image by a combination of the first image with the first spatially varying convolution function.

13. A method as claimed in claim 2, in that the following steps are carried out for obtaining an $(n+1)^{th}$ improved image in an iterative process, in which process the following steps are performed:
   a) determination of an $(n+1)^{th}$ spatially varying convolution function from the $n^{th}$ image and the optical parameters, and
   b) determination of the $(n+1)^{th}$-image of the object by a combination of the $n^{th}$ image with the $n^{th}$ spatially varying convolution function.

14. A method as claimed in claim 3, in that the following steps are carried out for obtaining an $(n+1)^{th}$ improved image in an iterative process, in which process the following steps are performed:
   a) determination of an $(n+1)^{th}$ spatially varying convolution function from the $n^{th}$ image and the optical parameters, and
   b) determination of the $(n+1)^{th}$-image of the object by a combination of the $n^{th}$ image with the $n^{th}$ spatially varying convolution function.

15. A method as claimed in claim 13, characterized in that the method includes a step for non-linear coordinate transformation.

16. A method as claimed in claim 14, characterized in that the method includes a step for non-linear coordinate transformation.

17. A method as claimed in claim 2, characterized in that the optical parameters are attenuation coefficients.

18. A method as claimed in claim 3, characterized in that the optical parameters are attenuation coefficients.

19. A method as claimed in claim 4, characterized in that the optical parameters are attenuation coefficients.

20. A method as claimed in claim 5, characterized in that the optical parameters are attenuation coefficients.

* * * * *